US00PP09602P

United States Patent [19]

Fruehwirth

[11] Patent Number: Plant 9,602

[45] Date of Patent: Jul. 9, 1996

[54] POINSETTIA PLANT '3-91'

[75] Inventor: Franz Fruehwirth, Encinitas, Calif.

[73] Assignee: Paul Ecke Ranch, Inc., Encinitas, Calif.

[21] Appl. No.: 452,278

[22] Filed: May 26, 1995

[51] Int. Cl.[6] ..... A01H 5/00

[52] U.S. Cl. ..... Plt./86.1

[58] Field of Search ..... Plt./86.1

[56] References Cited

U.S. PATENT DOCUMENTS

P.P. 7,234 5/1990 Fruehwirth ..... Plt./86.1

P.P. 8,733 5/1994 Fruehwirth ..... Plt./86.1

*Primary Examiner*—James R. Feyrer

*Attorney, Agent, or Firm*—Arnold, White & Durkee

[57] ABSTRACT

Poinsettia '3-91' is a new cultivar, distinguished by blushed red flower bracts and self-branching characteristics. '3-91' is a color sport of the bicolored poinsettia '135' (U.S. Plant Pat. No. 7,234) with the same flowering response and cultural requirements. The new plant produces a very desirable branched flowering pot plant.

1 Drawing Sheet

BACKGROUND OF THE NEW PLANT

This new poinsettia cultivar originated as a natural red blushed bracted sport of poinsettia '135' (U.S. Plant Pat. No. 7,234) in my greenhouse in Encinitas, Calif. It was selected because of its unusual flower bract color and self branching characteristics; traits which distinguish it from other poinsettia cultivars, and seem to make it a desirable plant for commercial greenhouse production. The bract color of '3-91' is distinctively different from the parent plant, poinsettia '135', which has a predominant white background with red splotches of various sizes and shapes randomly scattered over the bracts. '3-91' has a more uniform blush of red over the entire bract surface. Poinsettia '3-91' is also distinct from poinsettia '4-91' (U.S. Plant Pat. No. 8,733) in that the percent of bract area with the red blush is greater for '3-91'. The red pigment of '3-91' bracts is darker than '4-91'.

After selection, '3-91' was vegetatively reproduced from stem cuttings for test purposes on Encinitas, Calif. By subjecting clones of this plant to successive generations of vegetative propagation, it was demonstrated that the distinctive characteristics of '3-91' held true from generation to generation.

DESCRIPTION OF THE PHOTOGRAPHS

Poinsettia '3-91' is illustrated in the accompanying color photographs. The upper photo is a side view of 3 single stem plants per pot in full flower. Evidence of self-branching can be seen in the flowering axillary branches beneath the upper canopy of bracts.

The lower photo is a top view of the same plants showing flower and bract formation.

DESCRIPTION OF THE PLANT

The following is a detailed description of this new poinsettia as observed in Encinitas, Calif., U.S.A. during December 1992. Observations were recorded from flowering plants, grown as 3 single stem plants per pot. The pot was 14 cm in diameter and 11 cm in height. Color designations are compared to the 1986 edition of R.H.S. Colour Chart, first published in 1966 by the Royal Horticultural Society, London, England.

THE PLANT

The following Table summarizes some of the differences between '3-91' and poinsettia '4 -91'.

TABLE 1

| Plant | '3-91' | '4-91' |
|---|---|---|
| Bract Color | Red blush with creamy white background | Creamy white with pinkish-red blush |
| Red Bract Color | RHS 46B | RHS 46C |
| Flower filaments and stigmas | Reddish | Pink |

Origin: Naturally occurring sport of Poinsettia '135' (U.S. Plant Pat. No. 7,234).

Classification:

*Botanic.*—*Euphorbia pulcherrima* Willd.

*Common name.*—Poinsettia.

*Cultivar name.*—'3-91'.

Form: Shrub.

Height: Medium.

Growth habit: As a single stemmed plant, upright and vigorous with self-branching side shoots. The growth habit and cultural requirements appear to be the same as for the parent, poinsettia '135'. The application of a chemical growth retardant may be needed to restrict height for commercial pot plant production. I observed 3 unpinched plants in a pot with an overall height of 40 cm and an overall width of 44 cm. The bract diameter of individual flowers was 32 cm.

Branching: Axillary branches will develop and terminate in a flower without pinching. However, it is usually desirable to pinch '3-91' before flower induction and remove all terminal dominance. Then, all axillary branches will develop uniformly and at a faster rate.

Growth rate: Rooting of stem cutting occurs in 12–18 days under intermittent mist. The plant will flower in about ten weeks under continuous long night conditions and night temperatures of about 16°–18° C. In my greenhouse in Encintas, Calif., both the parent, poinsettia '135' and the sport '3-91' reached full maturity on December 4.

Foliage: The foliage is clean and uniformly green from bottom to top of the plant. The leaves are of medium size, leaf blades typically being 13–14 cm long and about 9 cm wide with leaf petioles 4–5 cm long.

*Leaf shape.*—Typical leaves are ovate with acute to obtuse bases and acuminate tips. Leaf margins are mostly entire or occasionally lobed with 1 indentation on each side of the leaf blade.

*Color.*—Upper side — Green, near RHS 147A. Under side — Green, near RHS 147B.

*Retention.*—The foliage lasts extremely well even under low light intensities in the consumer's home.

Bracts: Generally there are 15–18 red blushed bracts of various sizes subtending the cyathia. The primary bracts are large, have blades typically 18–21 cm long and 12–14 cm wide with petioles 5–6 cm long. Secondary bracts are smaller and of various sizes with bract petioles 2–3 cm long.

*Shape.*—Primary bracts are ovate with acute bases and acuminate tips. Primary bracts are lobed with 1 distinctive indention on either side of the bract. Secondary bracts are elliptic and have entire margins.

*Color.*—Upper side — Red blush. Bracts have a creamy white layer of cells beneath the surface layer; color between RHS 155B-D. The surface cells have varying amounts of a red pigment near RHS 46B. The red pigment is more intense in the smaller secondary bracts, and more diluted in the larger primary bracts. This gives an overall appearance of an almost solid red color to the smaller, inner bracts and a lighter reddish blush to the outer large bracts. Under side — Creamy white, near RHS 155D, with a red tint near RHS 46B in the surface layer of cells.

Flowers: Generally 18–21 cyathia (flowers) are present when the plant is in full bloom. Each cyathium is about 7 mm long and 6 mm wide, green in color, and fringed with red at the distal end. A yellow nectar cup protrudes from the side of each cyathium. The flower pedicel is also green and about 4 mm in length. The stamens protruding from the cyathia are reddish. The anthers are bifurcate; the pollen is yellow and copious. The stigmas are greenish white and trifurcate.

*Nectar exudate.*—Present, abundant.

*Seed formation.*—Self-incompatible.

*Fertility.*—Not observed.

Post production: '3-91' is resistant to epinasty after being confined to shipping containers. The foliage and bract retention is good.

What is claimed is:

1. A new and distinct Poinsettia plant, substantially as herein shown and described, distinguished by its blushed red flower bracts and self-branching traits.

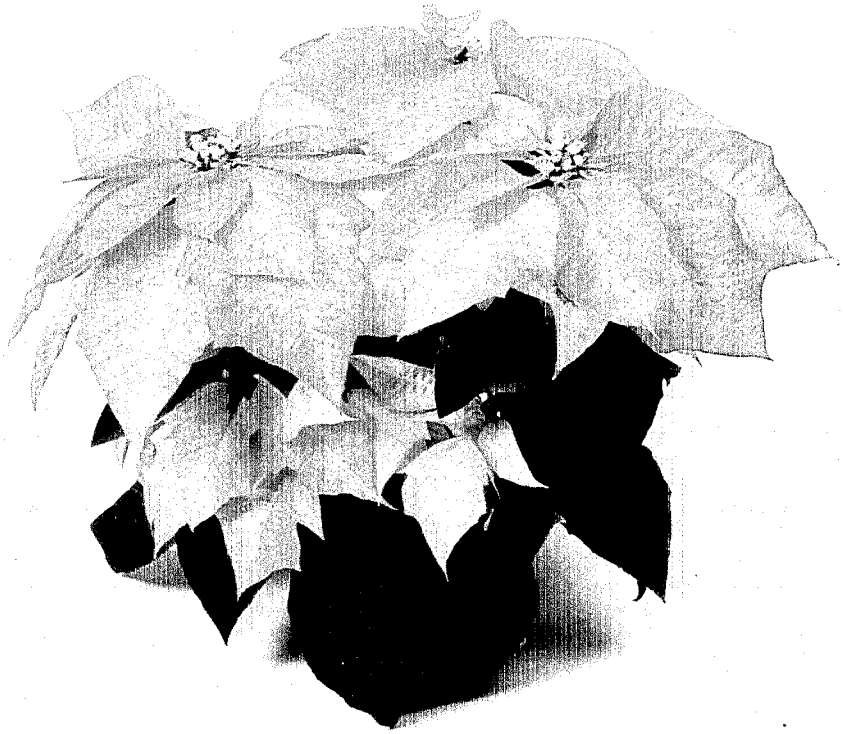
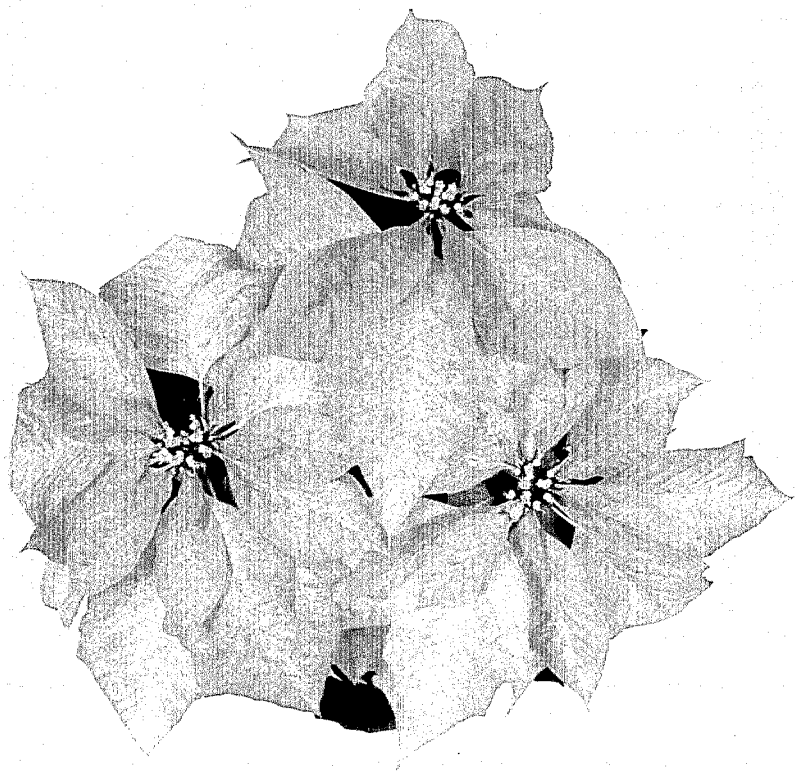

* * * * *